US008652493B2

(12) United States Patent
Apostol et al.

(10) Patent No.: US 8,652,493 B2
(45) Date of Patent: Feb. 18, 2014

(54) HYDROPHOBIC AGENTS STABLY DISPERSED IN OIL-IN-WATER EMULSIONS

(75) Inventors: Monica Apostol, Coram, NY (US); Liliana George, Centerport, NY (US); Charles Craig Tadlock, Islip Terrance, NY (US); Rachel Culhane, Wantagh, NY (US)

(73) Assignee: ELC Management, LLC, New York, NY (US)

( * ) Notice: Subject to any disclaimer, the term of this patent is extended or adjusted under 35 U.S.C. 154(b) by 2099 days.

(21) Appl. No.: 11/278,734

(22) Filed: Apr. 5, 2006

(65) Prior Publication Data

US 2007/0237798 A1    Oct. 11, 2007

(51) Int. Cl.
*A61K 8/06* (2006.01)
*A61Q 1/02* (2006.01)

(52) U.S. Cl.
CPC . *A61K 8/062* (2013.01); *A61Q 1/02* (2013.01); *Y10S 514/937* (2013.01); *Y10S 514/938* (2013.01)
USPC ............ 424/401; 424/400; 514/937; 514/938

(58) Field of Classification Search
CPC .......... A61K 8/062; A61Q 1/02; A61Q 17/04
USPC .......................................... 424/401; 514/938
See application file for complete search history.

(56) References Cited

U.S. PATENT DOCUMENTS

| 6,197,318 | B1 * | 3/2001 | Abe et al. ................. 424/401 |
| 6,306,805 | B1 | 10/2001 | Bratescu et al. |
| 6,455,058 | B1 * | 9/2002 | Sun et al. ................. 424/401 |
| 6,517,816 | B1 * | 2/2003 | Gonzalez et al. ........... 424/59 |
| 6,528,070 | B1 | 3/2003 | Bratescu et al. |
| 2004/0071653 | A1 | 4/2004 | Bratescu et al. |

FOREIGN PATENT DOCUMENTS

| WO | WO01/19507 | 3/2001 |
| WO | WO02/080864 | 10/2002 |

OTHER PUBLICATIONS

PCT International Search Report; International Application No. PCT/US07/060132; Completion Date: Oct. 10, 2007; Date of Mailing: Oct. 10, 2007.
PCT Written Opinion of the International Searching Authority, or the Declaration; Completion Date: Oct. 10, 2007; Date of Mailing: Oct. 10, 2007.
Grant Industries Product specification for Micro LA-20 (last modified Jul. 11, 2005); accessed Jan. 12, 2006; two pages.
Cosmetics & Toiletries (online version) vol. 121, No. 3 Mar. 2006, pp. 28,30-31,34-36 (particularly the box on p. 30).
Surfactant Chemisry J Eastoe, Chapter 3 Microemulsions, pp. 59-63; May 2003; UK; accessed at http://www.chm.bris.ac.uk/pt/eastoe/Surf_Chem/.

* cited by examiner

*Primary Examiner* — Daniel Sullivan
*Assistant Examiner* — Barbara Frazier
(74) *Attorney, Agent, or Firm* — Peter Giancana

(57) ABSTRACT

The present invention pertains to oil-in-water emulsion compositions having hydrophobic materials stably dispersed therein and methods for making such. The preferred method of making the emulsion compositions the formation of two O/W emulsions. A first O/W emulsion is for wetting or otherwise pre-treating the hydrophobic components. Thereafter, the first emulsion is added to a second O/W emulsion after the second emulsion has been formed. Both emulsions use a ternary surfactant blend of cationic, anionic and bridging surfactants, making the finished product a double or "binary-CAN" emulsion system. Generally, the system has a bi-modal oil droplet distribution.

17 Claims, 1 Drawing Sheet

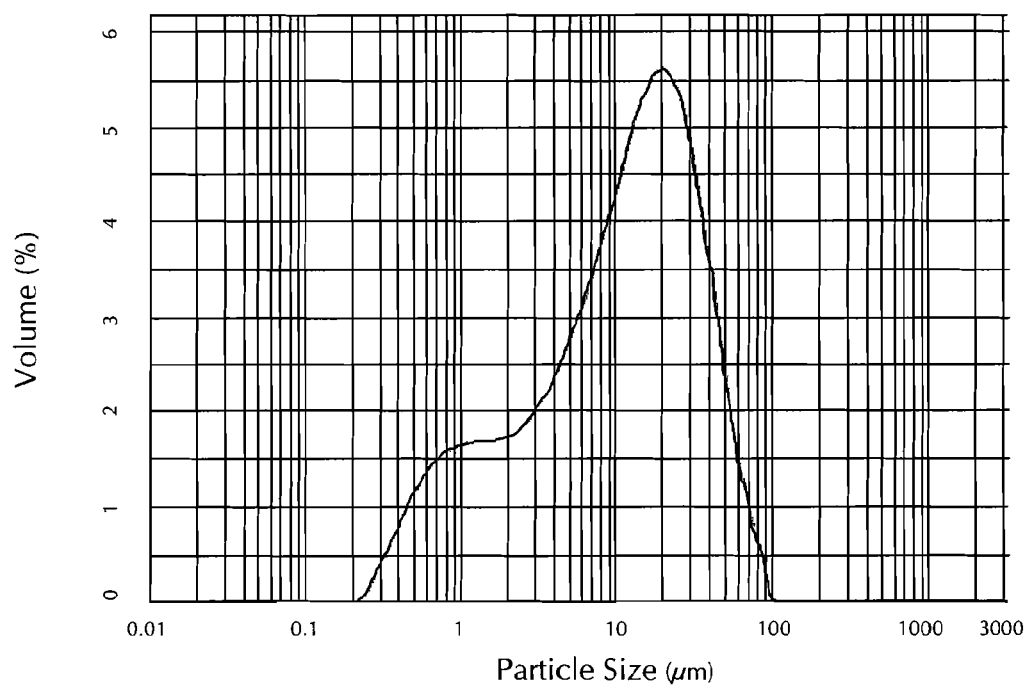

HYDROPHOBIC AGENTS STABLY DISPERSED IN OIL-IN-WATER EMULSIONS

FIELD OF THE INVENTION

The present invention pertains to cosmetic and dermatologic emulsion compositions, specifically to ternary-surfactant, oil-in-water emulsions (O/W) wherein one or more hydrophobic components is stably dispersed in the preformed emulsion.

BACKGROUND

In general, stable emulsion systems require the use of surfactants to reduce the surface energy at an interface between a water phase and an oil phase. Many such surfactants, or emulsifiers, are known. Some types of emulsifiers, more than other types, create emulsions of greater stability. For example, it is well known that O/W emulsions achieve greater stability if the emulsifier is anionic, that is a lipophilic tail attached to a hydrophilic end-group, the end-group having a net negative charge. A number of lipophilic tails surround and align in the direction of an oil droplet while the hydrophilic end groups extend out into the continuous water phase, away from the oil droplet. Thus, the outer most surface of the droplet complex is negatively charged. This causes droplets to repel each other and inhibits their coalescence, which would otherwise destabilize the emulsion. As an example, a formula for a stable emulsion with anionic emulsifier is shown in table 1. One drawback of this type of emulsion stabilization is that the anionic emulsifier cannot be introduced into the system by simple addition. Rather, the anionic emulsifier must be formed in situ. This is generally done by adding a non-polar precursor to the oil phase and a polar precursor to the water phase. Another drawback is that water-in-oil (W/O) emulsions cannot be stabilized in this manner.

TABLE 1

|  | percent |
| --- | --- |
| water | 58.05 |
| glycerine | 6.00 |
| sodium stearoyl glutamate (anionic emulsifier) | 2.60 |
| disodium EDTA | 0.10 |
| phenoxyethanol | 0.25 |
| isononyl isononanoate | 3.00 |
| denatured alcohol | 15.00 |
| dimethicone | 15.00 |

On the other hand, cationic emulsifiers are not generally used to stabilize an O/W emulsion. So, for example, an O/W emulsion having the formula shown in table 2, (the same as table 1, except for the emulsifier) is not stable at room temperature, even over a relatively short time. For this reason, cationic emulsifiers are not generally included in O/W emulsion systems.

TABLE 2

|  | percent |
| --- | --- |
| water | 58.05 |
| glycerine | 6.00 |
| isostearamidopropyl dimethylamine (cationic emulsifier) | 2.60 |
| disodium EDTA | 0.10 |
| phenoxyethanol | 0.25 |
| isononyl isononanoate | 3.00 |
| denatured alcohol | 15.00 |
| dimethicone | 15.00 |

Non-ionic emulsifiers may also be used to increase emulsion stability. Non-ionic emulsifiers introduced into an emulsion by simple addition will migrate to the water-oil interface and lower the interfacial energy, thereby making the emulsion more stable. Low HLB non-ionic emulsifiers will generally stabilize W/O emulsions, while high HLB emulsifiers will generally stabilize O/W emulsions. Table 3 is an example of a stable O/W emulsion using non-ionic emulsifiers.

TABLE 3

|  | percent |
| --- | --- |
| water | 72.80 |
| glycerine | 6.00 |
| phenoxyethanol | 1.00 |
| glyceryl stearate (non-ionic emulsifier) | 3.00 |
| cetyl alcohol (non-ionic emulsifier) | 2.20 |
| dimethicone | 15.00 |

Conventional Incorporation of Hydrophobic Agents—

It is well known that if hydrophobic agents are to be incorporated into O/W emulsions, the hydrophobic agents should be added to the oil phase prior to forming the emulsion. This is true in general and specifically of those color cosmetic emulsions that employ hydrophobic pigments. Generally, adding the hydrophobic agents to a preformed emulsion does not work, as the hydrophobic agents are not miscible in the external aqueous phase. For example, when hydrophobic pigment was added to the stable preformed O/W emulsion of the formula shown in table 1 (having anionic emulsifier), the result was that the pigment could not be dispersed and the composition was not stable. The same is true when hydrophobic pigment was added to the stable, preformed O/W emulsion of the formula shown in table 3 (having nonionic emulsifier).

Conventionally, when an O/W application calls for hydrophobic pigments, a pigment grind is made in advance and thereafter dispersed in an oil phase, prior to forming an emulsion. A typical pigment grind may comprise a simple mixture of hydrophobic pigment, oil and lecithin. The liquid portion of the grind "pre-wets" the pigments, making their incorporation into the oil phase easier. Alternatively, sometimes it may be possible to pre-treat a hydrophobic agent to make the agent "less hydrophobic," but this pretreatment step may not be desirable for a number of reasons. Pretreatment adds cost. It may interfere with the effectiveness of the hydrophobic agent. It may render the composition irritating to the skin. Such pretreatments are not available in all cases where one might like to use a hydrophobic ingredient. The present invention avoids these difficulties.

Generally, the internal phase droplets do not all have the same diameter, but the emulsion may be characterized as a range of droplet sizes about an average diameter. Emulsions are somewhat imprecisely classified based on the internal phase droplet size and on whether the emulsion is monodisperse or polydisperse (i.e. having one or more peak droplet diameters). For example, macroemulsions, which are typically opaque with milky-white appearance, comprise particle sizes larger than about 200 nm. In a microemulsion, the average droplet diameter is between 10-200 nm, while nanoemulsions have an average particle diameter less than about 10 nm. Other sources may place the boundary between macro and microemulsions at about 50 or 100 nm. Other sources maintain that nanoemulsions have larger droplet sizes (50-200 nm) than microemulsions (5-50 nm), the distinguishing feature having more to do with the type of stability (i.e. microemulsions are thermodynamically stable while nanoemulsions are kinetically stable). At any rate, because of their small droplet size, nanoemulsions and microemulsions are generally clear. Microemulsions and nano emulsions typically employ an aliphatic alcohol as co-surfactant and it is known that the average oil droplet size in an O/W emulsion depends on the ratio of alcohol to other surfactant in the system. Increasing the ratio of alcohol to surfactant decreases the average oil droplet size, which also increases the dispersion of the oil droplets and uniformity of the internal phase.

Benefits and Drawbacks of O/W and W/O Color Cosmetic Emulsions—

Turning specifically to color cosmetic compositions, foundations and other color products may be implemented as W/O or O/W emulsions, each having strengths and weakness. O/W makeup emulsions have better mass to skin tone properties than W/O makeup emulsions. By "better mass to skin tone properties", we mean that the color of a makeup applied to skin more closely matches the color of the same makeup sitting in a container at ambient conditions. O/W makeup emulsions generally feel lighter, cooler and less greasy than W/O makeup. They are also, easier to remove. Furthermore, O/W systems generally have better break on the skin, i.e. the makeup spreads more easily and more evenly. On the other hand, W/O makeup emulsions have better or longer wear characteristics than O/W makeup emulsions, which often include a film former to improve wearability. W/O makeup emulsions also hold up to moisture better than O/W emulsions. The developer is faced with this trade-off between truer color and feel on the one hand and long wear on the other. A simple, inexpensive method for achieving the best of both in a single emulsion is unknown in the prior art. This is unlike the present invention wherein the superior wear of a W/O emulsion makeup is combined with the pleasant aesthetics and truer color of an O/W emulsion makeup.

Conventionally, the type of pigments used to impart color determines the type of emulsion used to implement the makeup. If hydrophobic pigments are used, then the emulsion is a W/O emulsion, having the pigment dispersed in the external, oil phase, prior to emulsification. To avoid agglomeration of the pigment and ensure a good dispersion in the final emulsion, the hydrophobic materials may be prepared as a sub-phase called a grind. In the grind, pigments are pretreated or "wet" to assist their incorporation into the emulsion. For example, for incorporation into an O/W emulsion, the pigment may be pretreated with lecithin and oil. The grind is subsequently added to the oil phase of the emulsion, prior to forming the emulsion and mechanical mixing or shearing means are employed to aid the dispersion of the pigments. In contrast, the pigment of the present invention is pretreated in a novel manner, and the pretreated pigment is added to the base emulsion, after the base emulsion has been formed.

CAN-Type Emulsions—

Ternary blend emulsifier systems are known. U.S. Pat. No. 6,528,070 (herein incorporated by reference, in its entirety) describes a so called "CAN" emulsifier system. This ternary emulsifier system comprises a cationic (the "C" in CAN), an anionic (the "A" in CAN) and a bridging surfactant. The bridging surfactant may be a non-ionic surfactant, hence the "N" in CAN. However, the bridging surfactant may also be an amphoteric surfactant or an ethoxamide. The bridging surfactant acts as a bridge between the cationic and anionic surfactants. The reference discloses the ratios and concentrations of each emulsifier for which the final emulsion is stable. Disclosed are emulsions in which the CAN emulsifier system comprises from 0.3% to about 15% of the emulsion and wherein each of the cationic, anionic and bridging surfactants form about 0.1 to about 8.0% of the weight of the emulsion. Further disclosed are CAN-type emulsions comprising particulate matter, as for example, sunscreens at 0.1% to 10% on a weight basis. The particulate matter may be, for example, inorganic sunscreens, powders, pigments, abrasives, coal tar, anti dandruff agents or a mixture thereof. This emulsifier system is described as being particularly useful in making stable O/W emulsions without the use of additional hydrophilic groups (such as ethylene oxides) on the anionic or cationic surfactants.

Furthermore, according to the reference, the emulsions and suspensions disclosed can be made by combining the ingredients in any order. Also, the reference briefly mentions that hydrophobic materials may be incorporated into CAN-type emulsions. Taken together, this would seem to indicate that a stable emulsion system can be arrived at by adding a hydrophobic material to a preformed O/W emulsion. Concerning example 8 of the '070 reference (shown below in table 4) it is said that "a stable o/w emulsion was obtained when the anionic, cationic, bridge system (1:1:1 mole ratio) was used as an emulsifier system for a sunscreen formulation." This formula is purported to be stable at 25.degree. C., 43.degree. C. and 50.degree. C., for at least thirty days. The reference does not explain how the sunscreen was made, that is, was the hydrophobic titanium dioxide (Micro LA-20) added to the oil phase, in a conventional manner, or was it added to the preformed O/W emulsion? Applicants performed the following experiment. Column three of table 4 is identical to example 8 of the '070 reference, except for the substitution of CAN-emulsion systems. The formula in column 3 was prepared in two ways; adding the hydrophobic pigment to the oil phase and adding the hydrophobic pigment to the preformed CAN-type emulsion. In either case, the emulsion was stable at ambient conditions for at least one month. So indeed, in this specific case, adding a hydrophobic material to a preformed O/W CAN-type emulsion was possible. However, as we shall see, the formula of example 8 of the '070 reference and the formula of table 4, column 3 do have limitations that are not readily disclosed in the '070 reference.

TABLE 4

|  | Ex. 8 percent | 3 percent | 4 percent | 5 percent | 6 percent |
|---|---|---|---|---|---|
| Total CAN system | 1.7 | 1.7 | 1.7 | 1.7 | 1.7 |
| Anionic surfactant (STCS370) | x | | | | |
| Cationic surfactant (BTC65NF) | x | | | | |
| Bridge surfactant (AMXLO) | x | | | | |
| Anionic surfactant | | x | x | x | x |
| Cationic surfactant | | x | x | x | x |
| Bridge surfactant | | x | x | x | x |
| Elefac I-205 | 15 | 15 | 15 | 15 | 15 |
| Kessco octylisononanoate | 15 | 15 | 15 | 15 | 15 |
| Micro LA-20 untreated $TiO_2$ | 10 | 10 | | | |
| Alkyl silane pigment | | | 10 | | |

TABLE 4-continued

|  | Ex. 8 percent | 3 percent | 4 percent | 5 percent | 6 percent |
|---|---|---|---|---|---|
| fluoro alcoholic phosphate pigment |  |  |  | 10 |  |
| dimethicone treated pigment |  |  |  |  | 10 |
| Carbopol Ultrez 10 | 0.3 | 0.3 | 0.3 | 0.3 | 0.3 |
| water | qs100 | qs100 | qs100 | qs100 | qs100 |
|  | stable | stable | unstable | unstable | unstable |

Acting against the teachings of the reference, applicants conjectured that there may be limitations not disclosed in the '070 reference. Applicant's undertook the following action. Column 4 is identical to column 3 except for the substitution of alkyl silane pigment for Micro LA-20 (hydrophobic titanium dioxide). The formula of column 4 was prepared by adding the hydrophobic material (Alkyl silane pigment) to a pre-formed CAN emulsion. The resulting product is not stable after any amount of time. This result was also achieved when the alkyl silane pigment was replaced with a fluoro-alcoholic phosphate pigment (column 5) or with a dimethicone treated pigment (column 6). In other words, the '070 reference is overly broad in its implications that hydrophobic materials can be incorporated into O/W CAN-type emulsions by combining the ingredients in any order. In fact, as just shown, it is not generally possible to add hydrophobic materials to a pre-formed O/W emulsion, even a CAN-type emulsion. The hydrophobic material hits the external water phase and thereafter does not find a stable arrangement in the system. Furthermore, even if hydrophobic materials had been added to the oil phase of the CAN O/W emulsion, prior to forming the emulsion, the resulting composition is not necessarily stable and not necessarily of a suitable quality. The use of a CAN-type emulsion system as described in the '070 reference does not guarantee that hydrophobic materials can be stably dispersed in an O/W emulsion. In contrast, the applicants have discovered a modified method for stably dispersing hydrophobic materials in CAN-type O/W emulsions.

That the formula of example 8 of the '070 reference could be made by adding the hydrophobic titanium dioxide to the pre-formed O/W CAN-type emulsion may have to do with the fact that the specific titanium dioxide (Micro LA-20, from Grant Industries, Elmwood Park, N.J.) is pre-treated in aluminum hydroxide (and) lauric acid. Aluminum hydroxide (and) lauric acid is an acid salt and known non-ionic surfactant. As discussed above, non-ionic emulsifiers introduced into an emulsion by simple addition will migrate to the water-oil interface and lower the interfacial energy, thereby making an emulsion more stable. So, a careful reading of the '070 reference confirms that there is no general method disclosed for incorporating hydrophobic materials into a preformed CAN-type O/W emulsion. In contrast, the present invention includes compositions and methods for stably dispersing hydrophobic materials into preformed CAN-type O/W emulsions.

Furthermore, as mentioned above, the '070 reference discloses that stable emulsions are formed when the CAN emulsifier system comprises from 0.3% to about 15% of the emulsion and wherein each of the cationic, anionic and bridging surfactants form about 0.1% to about 8.0% of the weight of the emulsion. The reference includes examples wherein the bridging surfactant is as low as 0.31% of the weight of the emulsion. Based on this, a person of ordinary skill in the art could not be expected to find a novel use for a CAN-type surfactant system wherein the bridging surfactant is 0.05% or lower. Nevertheless, the applicants have done so.

Objects

A main object of the present invention is to provide compositions having one or more hydrophobic agents stably dispersed in an O/W emulsion.

Another object of the present invention is to provide compositions that combine the aesthetic properties of O/W emulsions and the long-wearing properties of W/O emulsions.

Another object is to provide a method of making compositions that have one or more hydrophobic agents stably dispersed in a base O/W emulsion, wherein the step of dispersing the hydrophobic agents takes place after the base emulsion is formed.

Another object is to provide a novel method of pre-treating hydrophobic agents for dispersing in O/W emulsions.

DESCRIPTION OF FIGURE

The FIGURE is a plot of oil droplet sizes present in the composition of table 7. The plot shows a bimodal distribution, with peaks at about 1 and 20 microns.

SUMMARY

The present invention pertains to oil-in-water emulsion products that have one or more hydrophobic components stably dispersed therein and methods for making such. The preferred method of making compositions of the present invention requires the formation of two O/W emulsions. A first O/W emulsion is for wetting or otherwise pre-treating the hydrophobic components. Thereafter, the first emulsion, which incorporates the hydrophobic components, is added to a second O/W emulsion after the second emulsion has been formed. Both emulsions use a ternary surfactant blend of cationic, anionic and bridging surfactants, making the finished product a double or "binary-CAN" emulsion system. Generally, the system has a bimodal oil droplet distribution.

DETAILED DESCRIPTION

Throughout this specification, the terms "comprise," "comprises," "comprising" and the like shall consistently mean that a collection of objects is not limited to those objects specifically recited. Furthermore, regarding compositions according to the present invention, all recitations of percent levels are to be understood as being "about" that level, unless otherwise noted.

Throughout this specification, the term "CAN-type emulsion" refers to an emulsion having a ternary surfactant system that comprises anionic, cationic and bridging surfactants. However, the levels of any of these may generally be the same or different from the levels disclosed in the '070 patent.

The preferred method of making compositions of the present invention requires the formation of two CAN-type O/W emulsions. Hereinafter, we will refer to these two emulsions as the "grind emulsion" and the "base emulsion". While emulsions according to the present invention may have various applications, for demonstration purposes we stress color cosmetic compositions. While various hydrophobic elements may be incorporated into the emulsion, we focus, for demonstration purposes, on cosmetic pigments.

The Grind Emulsion—

As discussed above, in conventional O/W emulsions that incorporate hydrophobic pigments, the pigments may be prepared as a sub-phase called a grind, wherein the pigments are pretreated with, for example, lecithin and oil. In contrast, the hydrophobic pigments of the present invention are pretreated by being incorporated into a CAN-type O/W emulsion, and that emulsion is subsequently added to a base emulsion, after the base emulsion has been formed. Implementing the grind as a CAN-type O/W emulsion for subsequent incorporation into a base emulsion is new and has several advantages which will be discussed below. Note, that hydrophobic cosmetic pigments are generally associated with W/O emulsions. Therefore, the incorporation of hydrophobic pigments into O/W emulsions, especially as a pre-treatment step, is not obvious.

In table 5 are three examples of an O/W grind emulsion (shown before the addition of hydrophobic pigments) using the CAN surfactant system, three with alcohol and one without.

TABLE 5

| | phase | 1 percent | 2 percent | 3 percent |
|---|---|---|---|---|
| water | 1 | 58.55 | 73.05 | 58.05 |
| glycerine | | 6.000 | 6.00 | 6.00 |
| sodium stearoyl glutamate (anionic) | | 1.05 | 1.05 | 1.05 |
| isostearamidopropyl dimethylamine (cationic) | | 1.00 | 1.00 | 1.00 |
| behenyl betaine (bridging) | | 0.05 | 0.55 | 0.55 |
| disodium EDTA | | 0.10 | 0.10 | 0.10 |
| phenoxyethanol | | 0.25 | 0.25 | 0.25 |
| isononyl isononanoate | 2 | 3.00 | 3.00 | 3.00 |
| alcohol denatured | 3 | 15.00 | — | 15.00 |
| dimethicone | | 15.00 | 15.00 | 15.00 |

A necessary feature of the present invention is that the oil droplet size of the grind emulsion be about 2 µm average diameter or less, better still, about 1 µm or less, best about 0.7 µm or less. Successfully dispersing hydrophobic materials in the grind emulsion seems to depend on achieving the stated oil droplet size. This may be achieved by any means known in the art, for example, by using a microfluidizer or Niro machine. The formulae of table 5 were prepared as follows, but it is expected that any means of forming a CAN-type emulsion with the stated oil droplet size will work equally well in the final composition. In a main kettle, phase 1 ingredients were blended with propeller mixing while heating to 70-75° C. In a separate kettle, isononyl isononanoate (wickenol 151, an ester) was heated to 70-75° C. and thereafter, added to the main kettle and homogenized, with, for example, a Silverson® homogenizer. Subsequently, the contents of the main kettle were passed one time through a microfluidizer, which also cooled the mix to about ambient temperature. The wickenol 151 is optional and does not limit the present invention. A different ester may be used, one that is known to be suitable to the intended product application, or no ester may be used. Phase 3 was added to the main kettle with homogenizer. Thereafter, the contents of the main kettle were passed three times through the microfluidizer. At that point, a CAN-type emulsion having oil droplet size of about 0.7 µm maximum diameter had been formed. All that remains is to add the hydrophobic pigments, which are preferably added to the main kettle with simple propeller mixing.

Hydrophobic materials, for example, cosmetic hydrophobic pigments, may comprise anywhere from about 0.001 to about 50% of the grind emulsion. For example, one or more hydrophobic pigments may be added to the emulsion of table 5, column 1 in a ratio of 1 to 2, respectively. For example, one or more hydrophobic pigments may be added to the emulsion of table 5, column 2 in a ratio of 1 to 3, respectively. For example, one or more hydrophobic pigments may be added to the emulsion of table 5, column 3 in a ratio of 1 to 2, respectively. Titanium dioxide and iron oxides are common examples of cosmetic hydrophobic pigments.

Even though the hydrophobic pigments are added after the emulsion is formed, the pigments, nevertheless, uniformly disperse throughout the emulsion. Emulsifiers work by creating a charged surface around each oil droplet, which prevents two oil droplets from coalescing and thereby destabilizing the system. Between the surface of the oil droplet and the charged surface of the emulsifier, is a volume that is devoid of oil and water. It may be reasonable to assume that a ternary emulsifier system provides a larger volume around an oil droplet than a conventional unary emulsifier system, given the larger size of the ternary emulsifier molecule. Applicant's believe that the volume provided by the ternary emulsifier system is large enough to entrap hydrophobic particles of the grind phase. In this way, one or more hydrophobic particles become entrapped or otherwise stably associated with an oil droplet, even though the particles are not surrounded by the oil droplet, as in a more conventional emulsion. The entrapment of the hydrophobic particles seems to prevent the agglomeration of the particles. As long as the oil droplets are uniformly disbursed throughout the continuous phase, so too are the hydrophobic particles. Hydrophobic pigment particles at least as large as about 3.0 µm (iron oxides) have been stably disbursed in emulsions of the present invention. However, depending on the exact emulsifiers used in the CAN-system and on the exact oil droplet size, larger or smaller particles may be dispersed.

As noted above, the alcohol assists in controlling the oil droplet size, but alcohol also has the advantage of improving the dispersion of the hydrophobic pigments within the emulsion, as well as increasing the amount of pigment that may be dispersed. When alcohol is not present, propeller mixing required about five hours to disperse the pigments at the percent level shown. In other experiments, two hours of mixing was required to disperse 25% pigment load, when alcohol was not used. When alcohol is used, mixing time for dispersing the hydrophobic pigment was consistently about fifteen to thirty minutes, even for 33% or more pigment load. Furthermore, alcohol provides a skin conditioning benefit, i.e. pore minimizing. For all these reasons, the grind emulsion preferably comprises alcohol. Amounts at least as high as 15% or amounts similar to the amount of oil, have proved useful. The exact amount may be readily determined by trial and error based on the perceived benefit or lack thereof.

Note, in column 1 of table 5, that the bridging surfactant (behenyl betaine), is present at only 0.05% (and actually less than about 0.03% after the hydrophobic materials are added). Although its presence in this CAN-type emulsion is critical, the amount is at least two times lower than any amount disclosed in the '070 patent and at least six times lower than any example disclosed in the '070 patent. Nevertheless, prior to adding the pigment, this emulsion is stable, even with an amount of bridging surfactant that is more than two times lower than taught by the '070 patent. While the choice of bridging surfactant may play some role, applicants believe the stability of this emulsion is enhanced by having an oil droplet size of about 2 µm average diameter or less. Thus, while the emulsion of column 1 is a CAN-type emulsion, it is nonetheless novel over the '070 patent and its use in the overall composition is non-obvious. In columns 2 and 3 of table 5, the bridging surfactant is about ten times greater than column 1, which is more in line with the disclosure of the '070 patent.

Furthermore, the successful dispersion of hydrophobic pigment seems particularly to be affected by the level of cationic emulsifier. It has been observed that cationic emulsifier may be present in the grind emulsion in a range of about 0.46 to 3.00%. If the cationic emulsifier goes below about 0.46%, there may not be enough structure within the emulsifier system to disperse significant quantities of hydrophobic materials. For example, cosmetic hydrophobic pigments may comprise anywhere from 0.001 to 50% of the grind emulsion. It has been observed that if the cationic emulsifier level is lower than about 0.46%, than satisfactory dispersion of 25-50% hydrophobic pigment is not achieved. Preferably, the range of cationic emulsifier is about 0.46 to 3.00%, more preferably it is 0.75 to 2.00% and most preferably it is about 1.00%. 1.00% seems to be adequate for dispersing typical quantities of hydrophobic pigments into a preformed O/W CAN-type emulsion. Additionally, the ratio of cationic emulsifier to anionic and bridging emulsifier is important. The applicants have observed that a molar ratio of anionic to bridging to cationic surfactant of about 1:≥0.2:≤0.5 was adequate to disperse some, but not all hydrophobic pigment. Thereafter, applicants determined that the most efficient thing to do was to tweak the cationic emulsifier. Raising the anionic to cationic emulsifier ratio to about 1:≤1, produced significantly better results. Therefore, for the grind emulsion, ratios of 1:≥0.2:≤0.5 may be useful, but preferred are ratios of about 1:≥0.2:≤1. This is somewhat unexpected in light of what was said above, about cationic emulsifiers being unsuitable for stabilizing conventional O/W emulsions and therefore cationic emulsifiers are not generally included in O/W emulsion systems. In contrast, in the present invention, the dispersion of hydrophobic pigments seems particularly dependent on the level of cationic emulsifier. It may be that when the anionic to cationic emulsifier ratio becomes too great, then the volume around each oil droplet is insufficient to entrap hydrophobic particles. This makes sense, in that excessive amount of anionic emulsifier over cationic emulsifier would tend to make the system behave more and more like a conventional unary emulsifier system. Therefore, unexpectedly, cationic emulsifier plays a critical role in dispersing hydrophobic materials in O/W emulsions.

The grind emulsion is water-thin, preferably having no thickener. Even though mechanical mixing can disperse the hydrophobic pigment throughout the emulsion (due to the pigment becoming entrapped in the emulsifier network), the water-thin grind emulsion cannot indefinitely suspend the pigment-laden oil droplets once mixing has stopped. At room temperature, pigment-laden oil droplets may precipitate within about 2 hours and certainly within 30 days. However, even when the oil droplets fall out of suspension, agglomeration of the pigments (or other hydrophobic materials) does not occur due to the entrapment of these materials in the emulsifier network. This enables the present invention to make use of what appears to be an otherwise unstable pigment suspension. In general, it may be possible to use thickener to stabilize the grind emulsion, but, a thickened grind emulsion would be more difficult, if at all possible, to incorporate into the main emulsion (see below). Therefore, the grind emulsions of the present invention, preferably have little or no thickener and the dispersions of table 5 constitute a new and non-obvious pretreatment of hydrophobic materials prior to their incorporation into a stable, "base" O/W emulsion.

The Base Emulsion—

Another step in making an O/W emulsion according to the present invention is the making of a stable base emulsion. Like the grind emulsion, the base emulsion is also a CAN-type emulsion. Unlike the prior art, a base emulsion according to the present invention is formed prior to adding the hydrophobic grind (i.e. grind emulsion). The hydrophobic grind is not added to the oil phase of the base emulsion, as a person of ordinary skill in the art might expect. Rather, it is added to a preformed base emulsion. This is unlike anything in the prior art, where it is understood that if hydrophobic agents are to be incorporated into an emulsion, the hydrophobic agents should be dispersed in an oil phase prior to forming the emulsion. This convention has been true in general and specifically of those color cosmetic emulsions that employ hydrophobic pigments. Generally, adding the hydrophobic agents to a preformed emulsion does not work, and this was shown to be the case when the emulsifier is anionic (see table 1) or nonionic (see table 3). It was further noted above, that cationic emulsifier (see table 2) could not generally produce a stable O/W emulsion, let alone one with hydrophobic pigments. Nevertheless, if a CAN-type emulsifier system as disclosed herein is used, then it is possible to make stable O/W emulsions having hydrophobic pigments, wherein the hydrophobic pigments are dispersed after the base emulsion is formed.

Table 6 is an example of a base emulsion according to the present invention.

TABLE 6

|  | phase | percent |
|---|---|---|
| water | 1 | 40.09 |
| glycerine |  | 6.00 |
| sodium stearoyl glutamate (anionic) |  | 1.06 |
| isostearamidopropyl dimethylamine (cationic) |  | 1.00 |
| behenyl betaine (bridging) |  | 0.55 |
| disodium EDTA |  | 0.10 |
| phenoxyethanol |  | 0.50 |
| skin conditioning/preparation agent(s) |  | 4.70 |
| isononyl isononanoate | 2 | 1.00 |
| alcohol denatured | 3 | 15.00 |
| dimethicone |  | 30.00 |

The formula of table 6 may be prepared in a manner similar to the grind emulsion. Here, however, the oil droplet size of the base emulsion may range from about 1 μm to about 100 μm average diameter. The formulae of table 6 was prepared as follows, but it is expected that any means of forming a CAN-type emulsion with the stated oil droplet size will work equally well in the final composition. In a main kettle, phase 1 ingredients were blended with propeller mixing while heating to 70-75° C. In a separate kettle, isononyl isononanoate (wickenol 151, an ester) was heated to 70-75° C. and thereafter, added to the main kettle and homogenized, with, for example, a Silverson® homogenizer. Subsequently, the contents of the main kettle were passed one time through a microfluidizer, which included cooling to about ambient temperature. The wickenol 151 is optional and does not limit the present invention. A different ester may be used, one that is known to be suitable to the intended product application, or no ester may be used. Phase 3 was added to the main kettle with homogenizer. Thereafter, the contents of the main kettle were passed three times through the microfluidizer. At that point, a CAN-type emulsion having oil droplet size of about 20 μm average diameter had been formed.

The levels of anionic, bridging and cationic emulsifiers of the base emulsion are consistent with those disclosed in the '070 patent, however, like the grind emulsion, without any thickener the base emulsion may not be stable for a considerable period of time. Preferably, a considerable period is at least 30 days in ambient conditions. More preferably, a considerable period is at least one year in ambient conditions and most preferably, a considerable period is at least five years at ambient conditions.

At the discretion of the user, the base emulsion may be prepared as just described, without thickener, and then stored for later use or the base emulsion may be thickened. At this point, it is possible to add enough thickener to stabilize the suspension of oil droplets or some amount of thickener less than that. The example of table 6 has no thickener, the thickener being added at the time that the full emulsion composition is to be formed (see below).

In the formula of table 6, the skin conditioning and/or preparation agents are shown as belonging to one phase, but this need not be so. Cosmetic, dermatologic and pharmaceutic adjuvants may be added to any one or more appropriate phases in amounts that do not destabilize the formula. A convenient feature of the present invention is the ability to disperse hydrophilic materials in the same emulsion with hydrophobic materials. So while the benefits of hydrophobic pigments can be achieved with the feel of an O/W emulsion, compositions of the present invention may also incorporate the benefits of hydrophilic actives and cosmetic adjuvants. A wide range of cosmetically and pharmaceutically acceptable materials may be advantageously used to preserve or alter the physical properties of the composition in order to create for the user a unique and pleasurable sensorial experience and/or to provide a benefit to the skin. These materials include, but are not limited to, an effective amount of one or more of the following: abrasives, absorbents, antiacne agents, anti-ageing agents, antifungal agents, anti-inflammatories, antimicrobial agents, antioxidants, antiperspirants, astringents, biocides, chemical exfoliants, cleansers, colorants, deodorants, depilating agents, emollients, epilating agents, external analgesics, humectants, light-interacting agents, luster-imparting materials, make-up removers, pH adjusters, powders, rheological modifiers, shine-imparting materials, skin bleaching agents, skin conditioning agents, skin protectants, sunscreens, tanning agents and UV absorbers. Just about any cosmetic, dermatologic or pharmaceutic agent suitable for topical use is within the purview of this invention, the only requirement being that the emulsion must remain stable for a considerable period.

The Full Emulsion Composition—

The grind emulsion and base emulsion may be prepared and stored well in advance of assembling into a final emulsion composition. There may be cost benefits associated with doing this. At any rate, table 7 is an example of a full emulsion composition according to the present invention.

TABLE 7

|  | phase | 1 percent |
|---|---|---|
| base emulsion of table 6 | 1 | 62.46 |
| *Aristoflex ® HMB and possibly other thickeners/gellants | 2 | 1.54 |
| grind emulsion of table 5, column 3 including hydrophobic pigment mixed in a 2:1 ratio | 3 | 30.00 |
| spherical silica | 4 | 5.00 |
| boron nitride |  | 1.00 |

*Ammonium Acryloyldimethyltaurate/Beheneth-25 Methacrylate Crosspolymer, a polymeric thickener, available from Clariant.

To prepare a final O/W emulsion composition having hydrophobic materials dispersed therein, phase 2 (thickener/gellant) is added to phase 1 at ambient conditions, i.e. room temperature, pressure and humidity, with propeller mixing. Phase 2 is any suitable thickener/gellant in a quantity sufficient to suspend the oil droplets of the grind emulsion thereby making the full composition stable for a considerable period of time. This quantity of thickener/gellant may be arrived at by trial and error and/or is readily determined by a person of ordinary skill in the art.

When phase 2 has been thoroughly dispersed in phase 1, then the pigment grind (phase 3) is added to the phase 1 base emulsion at ambient conditions, with propeller mixing. This is in patentable contrast to the conventional manner of making pigmented emulsions, wherein a grind is added to the oil phase before the main emulsion is formed. The incorporation of the grind emulsion is preferably achieved without the use of conventional wetting agents, although nothing precludes the use of such. At this point, additional dermatologic or cosmetic adjuvants may be added to the composition to impart a benefit. In the example of table 7, spherical silica beads are added for improved spreading over the skin and boron nitride powder adds a soft and lustrous feel.

The oil droplet sizes in the grind emulsion and base emulsion are generally different. The grind emulsion requires the oil droplets to be about 2 μm or less while, in the base emulsion, oil droplets may be about 100 μm or less. Generally, then, a full formula composition of the present invention has a bimodal oil droplet distribution. This can be seen in the FIGURE, which is a plot of oil droplet sizes in the composition of table 7. Here, the grind emulsion peak is seen at about 1 μm and the base emulsion peak is seen at about 20 μm. The FIGURE provides graphical evidence that the emulsion compositions of the present invention have an internal structure that is unlike anything disclosed in the '070 reference. The oils of the grind emulsion and base emulsion may be the same or different. The oils may be any cosmetically acceptable oils. The feel, break, wear, mass-to-skin-tone or removability may be affected by the choice of oils. A person of ordinary skill in the art can, by routine experimentation and personal knowledge, select suitable oils to achieve the desired aesthetic and physical properties.

As mentioned, the base emulsion (phase 1) is generally not stable for more than 24 or 48 hours and certainly less than 30 days. However, after the addition of thickener (Aristoflex, in this example), the base emulsion is stable for at least two years. It is therefore alternately possible to redefine "base emulsion" to include a quantity of thickener sufficient to stabilize the base emulsion for a substantial period of time, say, at least thirty days; more preferably, at least two years; most preferably, at least five years. When the base emulsion includes a stabilizing amount of thickening agent, then the benefits of preparing the base emulsion in advance, may be increased. For example, a stabilized base emulsion, by itself, may represent an efficacious and marketable product. Thus, the costs of manufacturing the stable base emulsion may be distributed over more than one product.

The ternary emulsifier systems of the grind emulsion and base emulsion may be the same or different. They may use all, some or none of the same surfactants. Anionic, cationic and bridging surfactants that may be utilized according to the present invention are well known to the art. Partial listings of these may be found in McCutcheon's Detergents & Emulsifiers, herein, incorporated by reference herein and in U.S. Pat. No. 6,528,070. The feel, break, wear, mass-to-skin-tone or removability may be affected by the choice of surfactants. A person of ordinary skill in the art can, by routine experimentation and personal knowledge, select suitable surfactants to achieve the desired aesthetic and physical properties.

The completed product is a stable, CAN-type O/W emulsion with hydrophobic pigments stably dispersed therein. The finished product is stable for at least about thirty days, preferably two years, most preferably five years. The finished product combines the attributes of conventional W/O and O/W cosmetic emulsions. The use of hydrophobic pigments yields O/W cosmetics with improved wear, comparable to that of W/O emulsions, while retaining all of the positive attributes of O/W cosmetic emulsions (i.e. good mass-to-skin-tone, good feel and break, easier removal, etc.). The present invention represents a simple, inexpensive method for achieving the best of both types of cosmetic emulsions in a single composition. This is unknown in the prior art.

What is claimed is:

1. An O/W emulsion composition comprising:
   a preformed CAN-type O/W grind emulsion that has hydrophobic pigments dispersed therein, and oil droplets that have an average diameter of 2 μm or less; and
   a preformed CAN-type O/W base emulsion that has oil droplets that have an average diameter of 100 μm or less; wherein:
   the preformed grind emulsion is mixed with the preformed base emulsion, and the O/W emulsion composition has a bi-modal oil droplet distribution.

2. The emulsion composition of claim 1 wherein the hydrophobic pigments make up from 0.001 to 50% of the preformed CAN-type grind emulsion.

3. The emulsion composition of claim 2 wherein the hydrophobic materials are cosmetic pigments.

4. The emulsion composition of claim 1 wherein the preformed CAN-type grind emulsion comprises alcohol.

5. The emulsion composition of claim 1 wherein the preformed CAN-type grind emulsion comprises a bridging surfactant, the bridging surfactant being present at 0.03%-8.00% of the grind emulsion.

6. The emulsion composition of claim 1 wherein the preformed CAN-type grind emulsion comprises a cationic surfactant, the cationic surfactant being present at 0.46-3.00% of the grind emulsion.

7. The emulsion composition of claim 1 wherein the preformed CAN-type grind emulsion comprises anionic, bridging and cationic surfactants in a ratio of 1:≥0.2:≤0.5.

8. The emulsion composition of claim 1 wherein the preformed CAN-type grind emulsion comprises no thickening agent.

9. The emulsion composition of claim 1 wherein the base emulsion comprises oil droplets having an average diameter of at least 1 μm.

10. The emulsion composition of claim 9 wherein the base emulsion comprises cosmetic, dermatologic or pharmaceutic adjuvants.

11. The emulsion composition of claim 1 wherein the preformed CAN-type grind emulsion accounts for up to 30% of emulsion composition.

12. The emulsion composition of claim 1 further comprising at least one thickener.

13. The emulsion composition of claim 12 that is stable for at least thirty days at ambient conditions.

14. The emulsion composition of claim 1 wherein the CAN-type surfactant systems of the preformed CAN-type grind emulsion and the preformed CAN-type base emulsion comprise the same surfactants.

15. The emulsion composition of claim 14 where in the cationic surfactant is isostearamidopropyl dimethylamine, the anionic surfactant is sodium stearoyl glutamate and the bridging surfactant is behenyl betaine.

16. A method of making a stable O/W emulsion composition having hydrophobic materials stably dispersed therein, the method comprising the steps of:
    forming a CAN-type O/W grind emulsion that has hydrophobic pigments dispersed therein, and oil droplets that have an average diameter of 2 μm or less;
    forming a CAN-type O/W base emulsion that has oil droplets that have an average diameter of 100 μm or less; and
    adding the grind emulsion to the formed base emulsion, wherein the stable O/W emulsion composition has a bi-modal oil droplet distribution.

17. The method of claim 16 wherein the grind emulsion is added to the base emulsion without conventional wetting agents.

* * * * *